United States Patent [19]

Ressemann et al.

[11] Patent Number: 5,921,958

[45] Date of Patent: *Jul. 13, 1999

[54] INTRAVASCULAR CATHETER WITH DISTAL TIP GUIDE WIRE LUMEN

[75] Inventors: Thomas V. Ressemann, St. Cloud; Steven S. Hackett, Maple Grove; Peter T. Keith, Fridley, all of Minn.

[73] Assignee: SciMed Life Systems, Inc., Maple Grove, Minn.

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/708,553

[22] Filed: Sep. 6, 1996

Related U.S. Application Data

[60] Continuation of application No. 08/400,982, Mar. 7, 1995, Pat. No. 5,571,087, which is a division of application No. 08/209,616, Mar. 10, 1994, Pat. No. 5,395,332, which is a continuation of application No. 07/922,902, Jul. 31, 1992, abandoned, which is a continuation-in-part of application No. 07/833,099, Feb. 10, 1992, abandoned.

[51] Int. Cl.$^6$ ................................................. A61M 29/00
[52] U.S. Cl. ............................ 604/96; 604/98; 604/269; 604/280; 606/194
[58] Field of Search ................................ 604/96, 98, 95, 604/100–104, 264, 280, 97, 269; 128/656, 657, 772, 658; 600/194

[56] References Cited

U.S. PATENT DOCUMENTS

| Re. 32,348 | 2/1987 | Pevsner | 128/325 |
|---|---|---|---|
| 2,043,630 | 6/1936 | Raiche | 604/96 X |
| 2,225,762 | 12/1940 | Barnsteiner | 312/156 |
| 2,657,691 | 11/1953 | Nordstrom, Jr. | 128/303 |
| 2,687,131 | 8/1954 | Raiche | 128/349 |
| 2,912,981 | 11/1959 | Keough | 128/349 |
| 2,930,377 | 3/1960 | Cowley | 128/344 |
| 2,936,760 | 5/1960 | Gants | 128/349 |
| 3,225,762 | 12/1965 | Guttman | 128/214 |
| 3,976,720 | 8/1976 | Hammer et al. | 260/857 |

(List continued on next page.)

FOREIGN PATENT DOCUMENTS

| 0 344 530 A1 | 12/1989 | European Pat. Off. . |
|---|---|---|
| 0 365 993 A1 | 5/1990 | European Pat. Off. . |
| 0 368 523 A2 | 5/1990 | European Pat. Off. . |
| 0 416 662 A2 | 3/1991 | European Pat. Off. . |
| 0 416 734 A1 | 3/1991 | European Pat. Off. . |

(List continued on next page.)

OTHER PUBLICATIONS

"Direct Balloon to Spring Tip Bond for Sleek Crossing", SciMed Life Systems, Inc., made public on date even with or prior to Sep. 9, 1996, 1 page.

Schneider (USA) Inc., brochure entitled *Monorail–Piccolino Coronary Balloon Dilatation Catheter*, Oct. 1988, 2 pages.

(List continued on next page.)

*Primary Examiner*—Danton D. DeMille
*Attorney, Agent, or Firm*—Crompton, Seager & Tufte

[57] ABSTRACT

A catheter for use in angioplasty includes a shaft formed from an elongated metallic tube and has an inflatable balloon at its distal end. A plastic tube connects a distal end of the metallic tube to a proximal end of the balloon. The metallic and plastic tubes thus define a lumen for providing inflation pressure to the balloon. A metallic core member is attached to the metallic tube and extends distally therefrom through the plastic tube and balloon. The distal end of the balloon is sealably secured to the core member. A tip body is connected to the core member distally of the balloon, with a short guide wire lumen being defined on the tip body. The guide wire lumen is adapted to slidably receive a guide wire which then extends along the catheter exteriorly of the balloon.

6 Claims, 7 Drawing Sheets

U.S. PATENT DOCUMENTS

| | | | |
|---|---|---|---|
| 4,026,296 | 5/1977 | Stoy et al. | 604/96 |
| 4,085,757 | 4/1978 | Pevsner | 128/325 |
| 4,137,906 | 2/1979 | Akiyama et al. | 128/2 A |
| 4,213,461 | 7/1980 | Pevsner | 128/348 |
| 4,261,339 | 4/1981 | Hanson et al. | 128/1 D |
| 4,289,128 | 9/1981 | Rusch | 128/207.15 |
| 4,311,146 | 1/1982 | Wonder | 128/325 |
| 4,323,071 | 4/1982 | Simpson et al. | 128/343 |
| 4,327,709 | 5/1982 | Hanson et al. | 128/1 D |
| 4,346,698 | 8/1982 | Hanson et al. | 128/1 D |
| 4,386,604 | 6/1983 | Hershey | 128/718 |
| 4,413,989 | 11/1983 | Schjeldahl et al. | 604/96 |
| 4,468,224 | 8/1984 | Enzmann et al. | 604/247 |
| 4,561,439 | 12/1985 | Bishop et al. | 128/348.1 |
| 4,582,181 | 4/1986 | Samson | 128/348.1 |
| 4,597,755 | 7/1986 | Samson et al. | 604/96 |
| 4,638,805 | 1/1987 | Powell | 128/344 |
| 4,652,258 | 3/1987 | Drach | 604/53 |
| 4,662,368 | 5/1987 | Hussein et al. | 128/303.1 |
| 4,705,507 | 11/1987 | Boyles | 604/101 |
| 4,717,381 | 1/1988 | Papantonakos | 604/96 X |
| 4,721,117 | 1/1988 | Mar et al. | 128/772 |
| 4,748,982 | 6/1988 | Horzewski et al. | 128/344 |
| 4,762,129 | 8/1988 | Bonzel | 128/344 |
| 4,769,006 | 9/1988 | Papantonakos | 604/96 X |
| 4,771,776 | 9/1988 | Powell et al. | 128/344 |
| 4,771,777 | 9/1988 | Horzewski et al. | 128/344 |
| 4,771,778 | 9/1988 | Mar | 123/344 |
| 4,771,782 | 9/1988 | Millar | 128/637 |
| 4,790,315 | 12/1988 | Mueller, Jr. et al. | 128/344 |
| 4,796,642 | 1/1989 | Harris | 128/772 |
| 4,798,193 | 1/1989 | Giesy et al. | 128/7 |
| 4,798,598 | 1/1989 | Bonello et al. | 604/280 |
| 4,811,743 | 3/1989 | Stevens | 128/772 |
| 4,820,349 | 4/1989 | Saab | 128/344 |
| 4,821,722 | 4/1989 | Miller et al. | 128/344 |
| 4,824,435 | 4/1989 | Giesy et al. | 604/49 |
| 4,838,268 | 6/1989 | Keith et al. | 128/344 |
| 4,846,174 | 7/1989 | Willard et al. | 128/344 |
| 4,850,358 | 7/1989 | Millar | 128/637 |
| 4,873,983 | 10/1989 | Winters | 128/657 |
| 4,877,031 | 10/1989 | Conway et al. | 128/344 |
| 4,881,547 | 11/1989 | Danforth | 128/344 |
| 4,896,670 | 1/1990 | Crittenden | 606/194 |
| 4,906,241 | 3/1990 | Noddin et al. | 606/194 |
| 4,917,088 | 4/1990 | Crittenden | 606/194 |
| 4,921,478 | 5/1990 | Solano et al. | 604/53 |
| 4,928,693 | 5/1990 | Goodin et al. | 128/637 |
| 4,932,413 | 6/1990 | Shockey et al. | 128/657 |
| 4,940,062 | 7/1990 | Hampton et al. | 128/772 |
| 4,943,278 | 7/1990 | Enteneuer et al. | 604/96 |
| 4,944,745 | 7/1990 | Sogard et al. | 606/194 |
| 4,946,466 | 8/1990 | Pinchuk et al. | 606/194 |
| 4,947,864 | 8/1990 | Shockey et al. | 128/772 |
| 4,953,553 | 9/1990 | Tremulis | 128/637 |
| 4,964,409 | 10/1990 | Tremulis | 128/657 |
| 4,966,148 | 10/1990 | Millar | 128/637 |
| 4,976,720 | 12/1990 | Machold et al. | 606/194 |
| 4,988,356 | 1/1991 | Crittenden et al. | 606/192 |
| 4,994,032 | 2/1991 | Sugiyama et al. | 604/96 |
| 4,998,917 | 3/1991 | Gaiser et al. | 604/96 |
| 4,998,923 | 3/1991 | Samson et al. | 606/194 |
| 5,002,532 | 3/1991 | Gaiser et al. | 604/101 |
| 5,003,990 | 4/1991 | Osypka | 128/772 |
| 5,024,234 | 6/1991 | Leary et al. | 128/663.01 |
| 5,032,113 | 7/1991 | Burns | 604/96 |
| 5,034,001 | 7/1991 | Garrison et al. | 604/53 |
| 5,035,686 | 7/1991 | Crittenden et al. | 604/96 |
| 5,035,705 | 7/1991 | Burns | 606/194 |
| 5,040,548 | 8/1991 | Yock | 128/898 |
| 5,042,985 | 8/1991 | Elliot et al. | 606/192 |
| 5,047,045 | 9/1991 | Arney et al. | 606/194 |
| 5,050,606 | 9/1991 | Tremulis | 128/637 |
| 5,057,120 | 10/1991 | Farcot | 606/194 |
| 5,061,273 | 10/1991 | Yock | 606/194 |
| 5,061,738 | 10/1991 | Solomon et al. | 523/100 |
| 5,102,403 | 4/1992 | Alt | 604/280 |
| 5,131,407 | 7/1992 | Ischinger et al. | 128/772 |
| 5,135,535 | 8/1992 | Kramer | 606/194 |
| 5,154,725 | 10/1992 | Leopold | 606/194 |
| 5,156,594 | 10/1992 | Keith | 604/96 |
| 5,159,937 | 11/1992 | Tremulis | 128/772 |
| 5,180,367 | 1/1993 | Kontos et al. | 604/101 |
| 5,190,046 | 3/1993 | Shturman | 604/96 X |
| 5,387,225 | 2/1995 | Euteneuer . | |
| 5,571,087 | 11/1996 | Ressemann et al. | 604/96 |

FOREIGN PATENT DOCUMENTS

| | | |
|---|---|---|
| 0 441 384 A2 | 8/1991 | European Pat. Off. . |
| 0 479 730 A1 | 4/1992 | European Pat. Off. . |
| 0 332 649 B1 | 2/1993 | European Pat. Off. . |
| 0 282 143 B1 | 9/1993 | European Pat. Off. . |
| 591963 | 5/1924 | France . |
| 627 828 | 10/1978 | U.S.S.R. . |
| 1251 914 | 8/1986 | U.S.S.R. . |
| 2 078 114 | 1/1982 | United Kingdom . |
| WO 86/06285 | 11/1986 | WIPO . |
| WO 88/00844 | 2/1988 | WIPO . |
| WO 92/00775 | 1/1992 | WIPO . |

OTHER PUBLICATIONS

Adanced Cardiovascular Systems, Inc. *ACS RX Dilatation Catheters,* 1988, 2 pages.

Bjorn Nordenstrom, M.D., "New Instruments for Catheterization and Angiocardiography", *Radiology,* vol. 85, Jul.–Dec. 1965, pp. 256–259.

Declaration of Paul G. Yock, M.D., in Support of ACS's Opposition to Schneider's Motion for Preliminary Injunction, dated Nov. 27, 1989, filed Dec. 4, 1989, in Schneider (Europe) AG v. Advanced Cardiovascular Systems, Inc., No. C88–20742–WAI, United States District Court, Northern District of California (including Exhibits 1–7) made public on or date even with or prior to Sep. 6, 1996.

Exhibit 1 to Yock Declaration dated Dec. 4, 1989: Curriculum Vitae of Paul G. Yock, M.D., 5 pages.

Exhibit 2 to Yock Declaration dated Dec. 4, 1989: Written Description entitled "Single–Operator Angioplasty System", 5 pages.

Exhibit 3 to Yock Declaration dated Dec. 4, 1989: Copy of Slide Comparing the ACS RX© with the original Schneider Monorail©, 1 page.

Exhibit 4 to Yock Declaration dated Dec. 4, 1989: Ronald E. Vlietstra, M.B., Ch. B. et al., article entitled "PTCA Percutaneous Transluminal Coronary Angioplasty", 2 pages. Roger F.J. Shepherd, M.B., B. Ch. et al., article entitled "The History of Balloon Angioplasty", 3 pages.

Exhibit 5 to Yock Declaration dated Dec. 4, 1989: L.E. Afzelius et al., *Lakartidningen,* article entitled "Ballongdilatation Av Esofagusstrikturer En Ny Behandlingsmetod", vol. 79, No. 30–31 (1982), 3 pages, and English translation, 13 pages.

Exhibit 6 to Yock Declaration dated Dec. 4, 1989: Albert A. Moss, M.D. et al., *NMR, CT, and Interventional Radiology,* article entitled "Interventional Gastrointestinal Procedures", 8 pages.

Exhibit 7 to Yock Declaration dated Dec. 4, 1989: Copy of U.S. Patent No. 3,884,242 entitled "Catheter Assembly" in the name of Bazell et al., 11 pages.

Bjorn Nordenstrom, *Balloon Catheters For Percutaneous Insertion Into The Vascular System,* Department of Diagnostic Roentgenology, Karolinska Sjukhuset, Stockholm, Sweden, Mar. 2, 1962, pp. 411–416.

"USCI Lo Profile II Balloon Dilatation Catheters," C.R. Bard, Inc. 1987, 4 pages.

"Until someone does it, no one thinks it can be done," C.R. Bard, Inc. 1988, 4 pages.

The Ace, "Fixed–Wire Technology, Perfected", SCIMED Life Systems, Inc., made public on date even with or prior to Sep. 6, 1996, 4 pages.

The illustration labeled "Ace Corewire" is a detailed drawing of a corewire for use with the ACE catheter, made public on a date even with or prior to Sep. 6, 1996.

Press Release dated Aug. 28, 1989, SciMed Life Systems, Inc., 1 page.

Press Release dated Sep. 18, 1989, Schneider (USA), 1 page.

Press Release dated May 23, 1990, Schneider, 1 page. (Pfizer, New York, N.Y.).

Schneider, brochure entitled *The Monorail Piccolino,* made public on date even with or prior to Sep. 6, 1996, 4 pages.

Schneider, *Monorail System* instruction manual, made public on date even with or prior to Sep. 6, 1996, 7 pages.

Schneider–Shiley AG, *Monorail–Bonzel Coronary Dilatation System,* made public on date even with or prior to Feb. 6, 1996, 8 pages.

SciMed Life Systems, Inc. "Case Study: Ace Conformability Steerability", 1989, 1 page.

SciMed Life Systems, Inc. "Unibody Core Wire for Excellent Tip Response", 1 page.

Overlie et al., "Advances in Balloon Catheter Technology: Expanding Clinical Efficacy", SciMed Life Systems, Inc. 1989, 4 pages.

INTRAVASCULAR CATHETER WITH DISTAL TIP GUIDE WIRE LUMEN

RELATED APPLICATION

This is a continuation application of U.S. application Ser. No. 08/400,982, filed Mar. 7, 1995 Pat. No. 5,571,087 which is a divisional of U.S. application Ser. No. 08/209,616, filed Mar. 10, 1994, now U.S. Pat. No. 5,395,332, which is a continuation of U.S. application Ser. No. 07/922,902, filed Jul. 31, 1992 abandoned, which is a continuation-in-part of U.S. application Ser. No. 07/833,099, filed Feb. 10, 1992 abandoned.

BACKGROUND OF THE INVENTION

The present invention relates to the field of angioplasty. In particular, the present invention relates to an intravascular catheter, such as a dilatation balloon catheter, of the type which is advanced over a guide wire and which has a short guide wire lumen adjacent the distal end of the catheter.

Angioplasty procedures have gained wide acceptance in recent years as an efficient and effective methods for treating certain types of vascular diseases. In particular, angioplasty is widely used for stenoses in the coronary arteries, although it is also used for the treatment of stenoses in other parts of the vascular system.

The most widely used form of angioplasty makes use of a dilatation balloon catheter to treat a stenosis and thereby reestablish an acceptable blood flow through the artery. The dilatation catheter includes an elongated tubular shaft and an inflatable balloon carried at a distal end of the shaft. In operation, the catheter is inserted through a hollow guide catheter which has been previously introduced into a patient's vascular system from a location remote from the heart (e.g., femoral artery). The proximal end of the guide catheter remains outside the patient while the distal end of the guide catheter is positioned at the coronary artery ostium. A dilatation catheter is introduced into the proximal end of the guiding catheter and advanced to the distal end of the guide catheter. Then, by using fluoroscopy, the physician guides the dilatation catheter the remaining distance through the vascular system until the balloon is positioned across the stenosis therein. The balloon is then inflated by supplying fluid under pressure, through an inflation lumen in the catheter, to the balloon. The inflation of the balloon causes a widening of the lumen of the artery to reestablish acceptable blood flow through the artery. After a short inflation period (e.g., 30–90 seconds), the balloon is deflated and the arterial treatment evaluated to determine whether the procedure has reestablished an acceptable blood flow. The evaluation is conducted by introducing a radiopaque dye solution into the artery via the guiding catheter, and then observing the dye flow using fluoroscopy. If necessary, the dilatation procedure is repeated with the catheter balloon being re-inflated. In procedures in the peripheral vessels (vessels other than coronary vessels), a guide catheter may not always be used.

The placement of the dilatation balloon across a stenosis in a coronary artery can be a difficult procedure. Movement of the elongated dilatation balloon catheter (e.g., 135 cm) is achieved by manual manipulation of its proximal end outside the patient. The ability of a catheter to bend and advance through the vasculature is commonly referred to as the "trackability" of the catheter. "Pushability" refers to the ability of the catheter to transmit the longitudinal forces applied by the physician along the catheter shaft to advance the distal end of the catheter through a coronary artery to and across the stenosis. Preferably, a catheter has a low profile, and is relatively trackable and pushable.

One common type of dilatation catheter has a separate guide wire lumen in the catheter so that a guide wire can be used to establish the path through the stenosis. The dilatation catheter can then be advanced over the guide wire until the balloon on the catheter is positioned within the stenosis.

During an angioplasty procedure, it is sometimes desirable to replace an existing catheter with another catheter. In that instance, the physician prefers to maintain the position of the guide wire in the patient's vascular system relative to the stenosis as the catheter is withdrawn over the guide wire. In the event of an abrupt closure of a partially dilated lesion when the balloon catheter has been withdrawn after an initial dilatation, the wire will maintain the path through the lesion. Any significant or uncontrolled movement of the exposed guide wire is avoided, so that the guide wire does not become dislodged from its position across the lesion. In order to exchange a catheter with a guide wire lumen that extends the entire length of the catheter shaft, a longer exchange wire is sometimes exchanged for the standard guide wire, or a guide wire extension may be provided. The use of long exchange wires or guide wire extensions present a great length of guide wire outside the patient which must then be managed during the catheter exchange procedure. This not only proves awkward but typically requires two persons.

In one type of dilatation catheter, the guide wire lumen extends from a distal end of the catheter through the dilatation balloon and then exits the catheter at a point proximal of the balloon. To accomplish a catheter exchange using a catheter having a distal guide wire lumen, the initial catheter can be preloaded onto the guide wire before the guide wire is inserted into the guide catheter, or positioned on the proximal end of the guide wire once the guide wire has been introduced into the guide catheter. In either case, the guide wire is steered through the guide catheter, coronary vessel and across the stenosis. Then the proximal exposed portion of the guide wire (outside the patient) is grasped and the catheter is pushed distally to advance it along the guide wire and across the stenosis.

If a different dilatation balloon is then desired, the catheter is withdrawn without removing the guide wire from across the stenosis. First, the guide wire is grasped near the proximal end of the guide catheter. The catheter is then withdrawn, and when the proximal opening of the guide wire lumen is reached, the grasping hand is moved incrementally away from the proximal opening of the guide wire lumen on the catheter. The catheter is then incrementally withdrawn until the catheter is fully removed from the guide catheter and the guide wire is thus again exposed and accessible adjacent to the proximal end of the guide catheter. Once the initial catheter has been completely removed from the guide wire, a second catheter is loaded onto the guide wire by inserting the proximal end of the guide wire into a distal opening of the guide wire lumen in the second catheter. This second catheter is then advanced by "feeding" the catheter distally over the guide wire while holding the guide wire stationary. The proximal end of the guide wire will then emerge out of the proximal opening of the distal guide wire lumen and is accessible again for gripping by the physician. By now holding onto the exposed portion of the guide wire in this manner, the second catheter can then be advanced distally along the stationary guide wire to a desired position in the patient's vasculature.

Another type of catheter places the entire guide wire lumen adjacent the distal tip of the catheter (distally of the intravascular interoperative element (e.g., dilatation balloon) on the catheter). In a catheter design where the guide wire does not extend through the catheter balloon, it is important that the catheter structure provide sufficient rigidity along the catheter shaft and through the balloon (all the way to the distal tip of the catheter where the guide wire lumen is located), so that the catheter has the necessary pushability.

SUMMARY OF THE INVENTION

The present invention is an intralumenal catheter that has good pushability and trackability, has a small shaft diameter, and can be readily exchanged by a single angioplasty operator. The inventive catheter may be guided over a guide wire and has a guide wire lumen extending through only a distal portion of the catheter. In one embodiment of the present invention, the catheter has an elongated shaft with a proximal end and a distal end, with a proximal end of the shaft defined by a metallic tube. The shaft has a distal portion which is relatively more flexible than the proximal portion. A core member is connected to the metallic tube and extends along the distal portion of the shaft. A tip assembly is connected to a distal end of the core member, and includes a short guide wire lumen defined therethrough.

The core member thus reinforces the distal more flexible portion of the shaft in a manner that provides a relatively flexible distal shaft portion but yet prevents closure or kinking in the flexible part of the catheter. The core member allows the position of the inlet to the guide wire lumen to be placed distally of the metallic tube of the proximal shaft portion. In an embodiment of the present invention wherein the catheter has a dilatation balloon thereon adjacent the distal end of the shaft, the guide wire lumen is entirely distal of the balloon, and the proximal and distal portions of the shaft thus define an inflation lumen through which inflation pressure may be provided to the balloon. The core member extends from the metallic tube through the distal portion of the shaft and through the balloon thereon to provide axial rigidity to the entire distal shaft section. The guide wire lumen inlet is then disposed distally of the distal end of the balloon.

This combination advantageously permits placement of the guide wire lumen distal of the balloon while optimizing pushability and trackability in the catheter shaft via the combination metallic tube proximal portion and flexible distal shaft portion with core member therethrough. Thus, the length of the guide wire lumen may be minimized while retaining the overall responsiveness of the catheter. The core member prevents kinking of the inflation lumen which may occur due to the abrupt change from the relatively stiff metallic tube to the relatively flexible distal shaft portion. In this arrangement, the guide wire thus extends alongside and externally to the dilatation balloon and catheter, except for the very short guide wire lumen on the catheter distal of the balloon.

BRIEF DESCRIPTION OF THE DRAWINGS

The invention will be further described with reference to the accompanying drawings where like numbers refer to like parts in several views and wherein.

While the above identified drawing figures set forth several preferred embodiments, other embodiments of the present invention are also contemplated, as noted in the discussion. In all cases, this disclosure presents illustrated embodiments of the present invention by way of representation and not limitation. It should be understood that numerous other modifications and embodiments can be devised by those skilled in the art which fall within the scope and spirit of the principles of this invention. It should be noted that the figures have not been drawn to scale as it has been necessary to enlarge certain portions for clarity.

DETAILED DESCRIPTION OF THE PREFERRED EMBODIMENTS

Introduction

The intralumenal catheter of the present invention has a metallic tube as a proximal portion of its main shaft and has a very short guide wire lumen at the distal tip of the catheter. A metallic core member is connected to the metallic tube and extends through distal, more flexible portions of the catheter to the catheter's distal tip. The metallic tube and core member provide the necessary pushability for the catheter to permit its highly controlled advancement along a guide wire. The flexible distal portions of the catheter permit the catheter to negotiate the often tortuous vascular lumens, and the distal guide wire lumen allows the catheter to be used in conjunction with a guide wire which has already established a path to that area of the vascular system of interest.

Figures 1, 2:
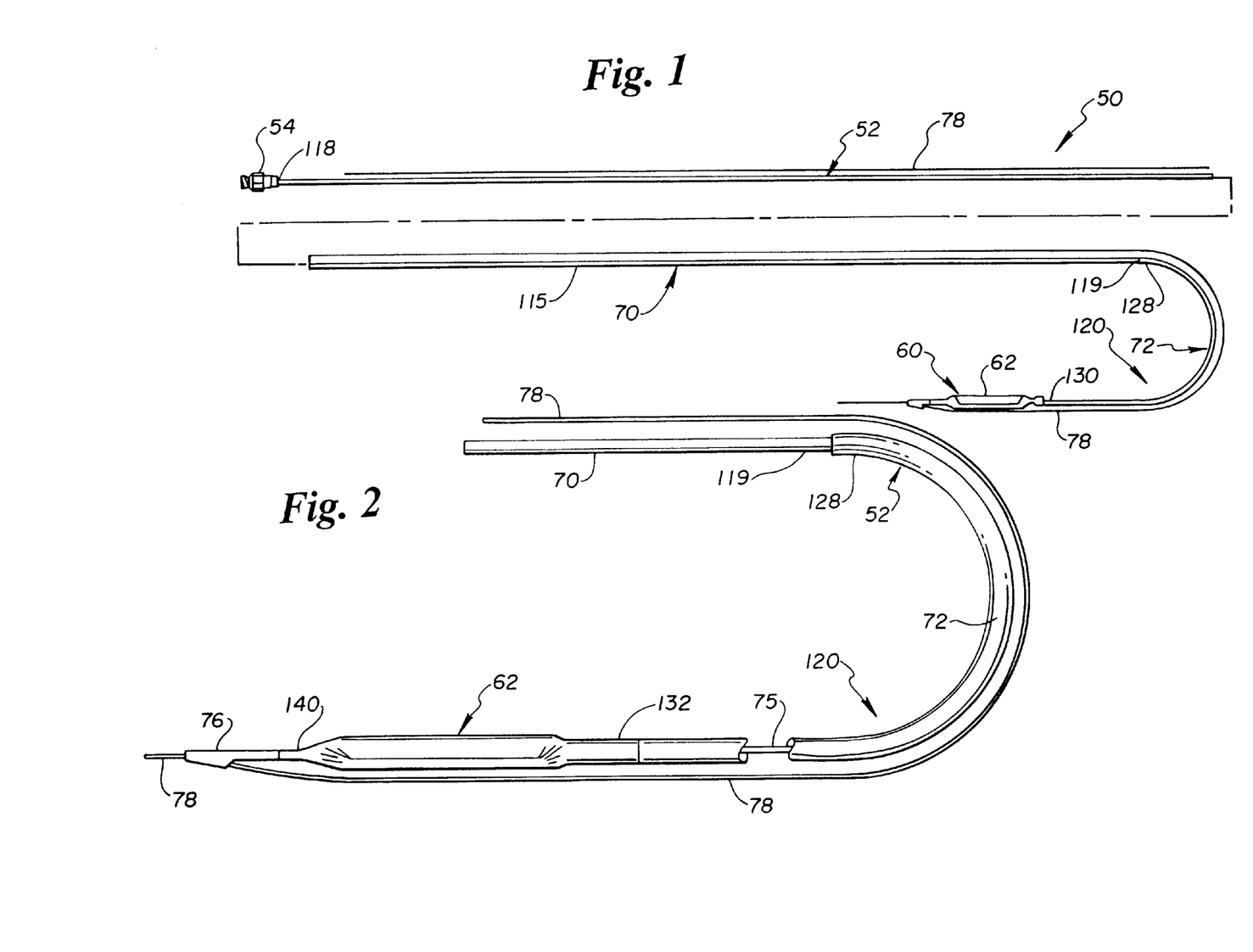
FIG. 1 is a plan view of an angioplasty balloon catheter of the present invention.
FIG. 2 is an enlarged plan view of a distal portion of the angiplasty balloon catheter of FIG. 1.

FIG. 1 illustrates an intralumenal catheter of the present invention, such as an angioplasty dilatation balloon catheter 50. The catheter 50 has a shaft indicated generally as shaft 52 which has a mating member 54 of a luer connector on its proximal end and an inflatable balloon 62 on its distal end. As shown more clearly in FIG. 2, the shaft 52 includes a first tubular segment 70 and a second tubular segment 72. The second tubular segment 72 is connected to a distal end of the first tubular segment 70 and extends distally therefrom. The balloon 62 (shown deflated in FIGS. 1 and 2) is connected to a distal end of the second tubular segment 72 and extends distally therefrom. A core member 75 extends longitudinally from a distal end of the first tubular segment 70 through the second tubular segment 72 and through the balloon 62 to a distal end thereof. The balloon 62 is bonded to the core member 75 proximally of the distal end of the core member 75. A distal tip body 76, which is connected to the core member 75 distally of the balloon 62, has a short (compared to the overall length of the catheter) guide wire lumen extending therethrough for slidable reception of a guide wire 78 (such as a 175 cm standard guide wire). Although the following description of the invention is directed to a balloon catheter, it will be appreciated by those skilled in the art that the invention may be used on other interventional catheters with lumenal or vascular interoperative devices, such as atherectomy devices, ultrasonic imaging and therapeutic catheters, laser catheters, stent delivery catheters, and perfusion catheters.

Catheter System Background

Figures 3A, 3B:
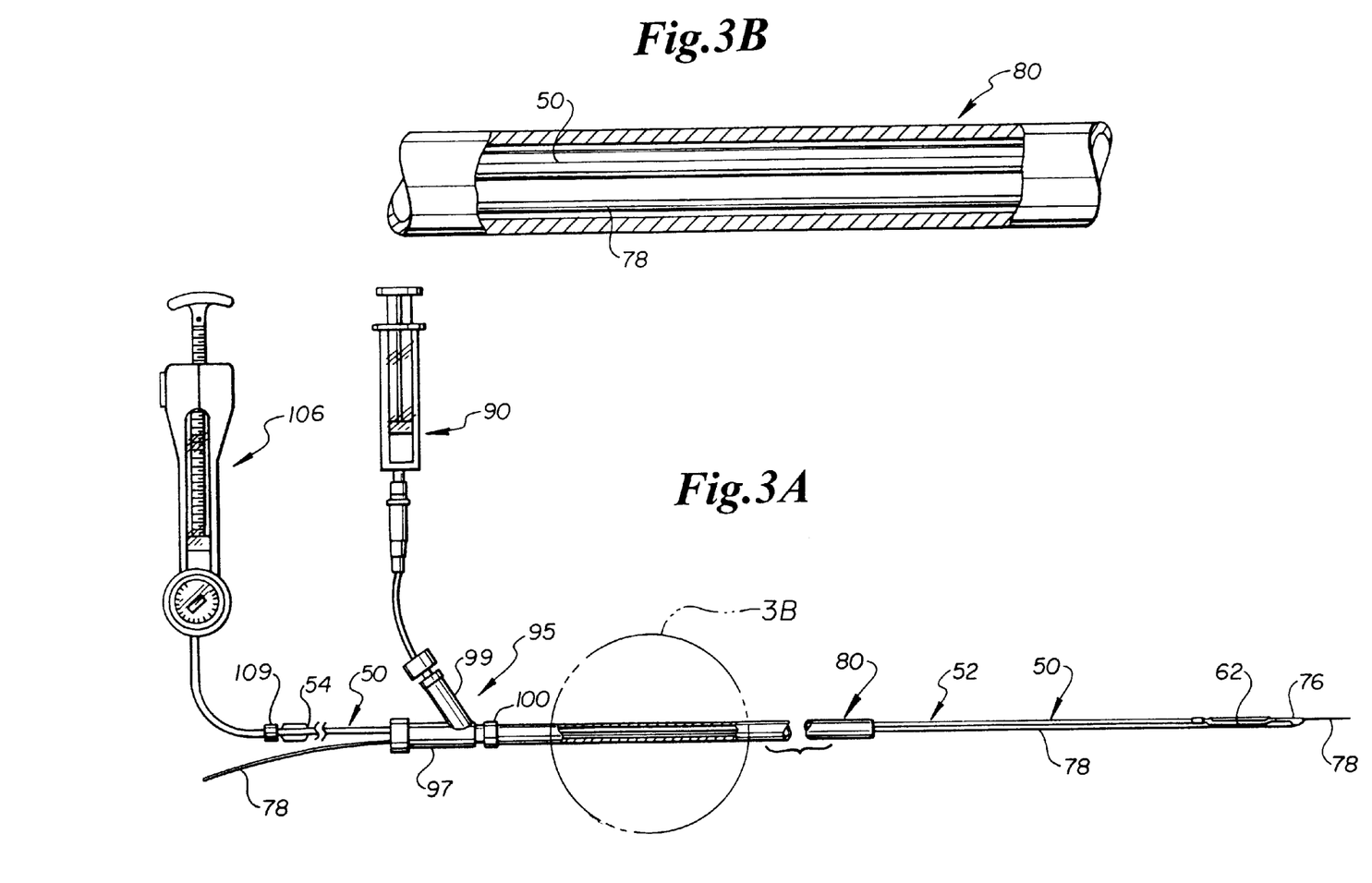
FIG. 3A is a plan view, shown in partial cross-section, of the angioplasty balloon catheter of FIG. 1 in operation with a guide catheter and guide wire.
FIG. 3B is a greatly enlarged sectional view of section 3B of FIG. 3A.

As shown in FIGS. 3A and 3B, the angioplasty dilatation balloon catheter 50 illustrated in FIGS. 1 and 2 is used in cooperation with a guide catheter 80. The guide catheter 80 is formed of an elongated flexible tube of approximately 100 cm in length. Both the catheter 50 and the guide wire 78 are longer than the guide catheter 80, with a typical catheter length of approximately 135 cm and a typical guide wire length of approximately 175 cm. In a typical coronary angioplasty procedure, the guide catheter 80 is inserted into the arterial system of a patient at the femoral artery and advanced until a distal end thereof is positioned at the ostium of the coronary artery to be dilated.

Once the guide catheter 80 is in place, the guide wire 78 is then aligned in the stenosed artery to a desired position through the stenosis. Then, the angioplasty dilatation balloon catheter 50 of the present invention is advanced along the guide wire 78 to position the inflatable balloon 62 across the stenosis.

As shown in FIGS. 3A and 3B, the angioplasty balloon catheter 50 of the present invention is inserted into the patient through the guide catheter 80 in cooperation with the guide wire 78. The balloon catheter 50 is slidably maintained on the guide wire 78 by the guide wire lumen of the distal tip body 76 (FIG. 2). The guide wire 78 is only entrained in the catheter 50 through the guide wire lumen. The balloon catheter 50 and the guide wire 78 are cooperatively advanced through the guide catheter 80 (either sequentially or simultaneously) to a distal end of the guide catheter 80, at the ostium of the coronary artery to be dilated.

Thereafter the guide wire 78, which is slidably maintained within the guide wire lumen on the tip body 76, is advanced into the coronary artery independently of the balloon catheter 50 to establish a path through the coronary artery and across the lesion. An angioplasty guide wire is designed to be steerable, and the slim profile of the guide wire permits the guide wire to be advanced through the obstructed area in order to establish a path therethrough for the catheter. Once the guide wire 78 is positioned across the obstructed area, the balloon catheter 50 is advanced along the guide wire 78 until the balloon 62 at the distal end thereof crosses the lesion in preparation of performing the dilatation procedure. As illustrated in FIGS. 3A and 3B, except for that portion of the guide wire 78 within the guide wire lumen, the catheter 50 and guide wire 78 extend side-by-side through the guide catheter 80 and vasculature system.

As shown in FIG. 3A, a syringe 90 is provided to introduce a radiopaque dye solution into the guide catheter 80 inserted into the patient. The radiopaque dye solution is inserted into and through the guide catheter 80 prior to the introduction of the balloon catheter 50 and the guide wire 78 by the syringe 90 to locate and evaluate the stenosis or obstruction via fluoroscopy in a conventional manner. The syringe 90 is connected to the guide catheter 80 by a conventional Y-adaptor 95 which has a primary longitudinal arm 97 and an extension arm 99. A luer connection 100 attaches the primary arm 97 of the Y-adaptor 95 to a proximal end of the guide catheter 80. The syringe 90 is connected to the extension arm 99 to introduce radiopaque dye solution through the Y-adapter 95 into the guide catheter 80. A compressible through-valve (not shown) is mounted on the proximal end of the primary arm 97 to permit the Y-adapter 95 to prevent back-bleeding and dye leakage.

The angioplasty balloon catheter 50 and the guide wire 78 extend through the guide catheter 80 and through the primary arm 97 of the Y-adaptor 95. An inflation/deflation device 106 is used to inflate/deflate the inflatable balloon 62 at the distal end of the catheter 50. The inflation/deflation device 106 includes a mating member 109 which is sealably connected to the mating member 54 at the proximal end of the catheter 50.

Once the balloon catheter 50 is positioned for dilatation, an inflation medium is introduced through the catheter 50 by the inflation/deflation device 106 to inflate the inflatable balloon 62. The inflation of the balloon 62 via the inflation/deflation device 106 causes radially directed stretching forces to be applied to the artery wall at the stenosis. This stretches the artery wall outwardly while slightly compressing the obstructing plaque forming the lesion to widen the lumen and provide a more acceptable blood flow therethrough.

The balloon 62 is only inflated for a short time (e.g., 30–90 seconds) and then a net negative pressure is applied through operation of the inflation/deflation device 106 to deflate the balloon 62. This procedure may be repeated as determined necessary by the physician, with the results monitored by further introduction of radiopaque solution and fluoroscopy. If it is determined that a different balloon catheter would be more effective in the vascular system treatment, the original balloon catheter 50 is withdrawn from the patient while the guide wire 78 remains in place across the stenosis. A second catheter having a guide wire lumen in its distal tip body is then loaded onto the proximal end of the guide wire 78 and advanced over the guide wire 78, through the guide catheter 80 and across the stenosis for further treatment.

The Main Shaft Section

The first tubular segment 70 is a relatively stiff tubular shaft. Preferably, the first tubular segment 70 is formed as a thin-walled, high-strength metallic tube 115 (see FIGS. 1, 4 and 5). Preferably, metallic tube 115 is a stainless steel tube structure, which is commonly referred to as hypodermic tubing or hypotube. A suitable hypotube has a nominal outer diameter of approximately 0.023 in. and a nominal inner diameter of approximately 0.017 in. The metallic tube is coated with a lubricious coating such as polytetrafluoroethylene to provide a slippery outer shaft surface and reduce frictional resistance to catheter advancement. A suitable coating thickness is about 0.0005 in. The metallic tube is approximately 112 cm long. As a tubular structure, the interior of the metallic tube 115 is hollow, and thus defines an inflation lumen 116 extending from a proximal end 118 of the metallic tube 115 to a distal end 119 of a metallic tube 115. Inflation lumen 116 provides a path through which inflation fluid is provided to and from the balloon 62.

The inherent high-strength nature of the metallic tube 115 also allows it to withstand the internal fluid pressure necessary for proper balloon catheter operation. The thin-walled metallic tube structure of tube 115 is stiff enough to provide the desired pushability, yet allows for a relatively small profile shaft of the catheter 50. However, the stiffness of such a tube does not allow it to properly negotiate the coronary arteries or the arch of the aorta. Thus, the distal portion of the catheter is formed from more flexible materials, as explained below.

The high column strength and thickness of a hypotube shaft also gives the catheter improved responsiveness. In other words, the balloon in the distal regions of the catheter moves more definitely (in a 1:1 relationship) with motions imparted at the catheter's proximal end by a physician to actually "sense" the pathway of the catheter's track. This improved responsiveness gives valuable information to the physician regarding the passage of the catheter to and through the lesions. The catheter is thus extremely responsive to the doctor's controlling movement of the catheter from its proximal end, while at the same time having a relatively small profile and enhancing catheter visualization via fluoroscopy.

Other materials, such as a super elastic alloy (otherwise known as a shape memory alloy) may be used for the metallic tube 115 of the first segment 70. For example, TINEL available from Raychem, Corp. (Menlo Park, Calif.) or a nickel-titanium shape memory alloy available from Shape Memory Applications, Inc. (Sunnyvale, Calif.) may be used as a metallic tube material. It will be recognized by those skilled in the art that other relatively stiff materials may also be used for the metallic tubing component of the first tubular segment 70. For example, a braided polyimide or other relatively rigid composite material may be used.

The Catheter Distal Shaft Section

The second tubular segment 72 and core member 75 therein in combination define a distal shaft section 120 which extends distally from the metallic shaft section (first tubular segment 70) to the balloon 62. The second tubular segment 72 is more flexible than the first tubular segment 70. In an exemplary embodiment, the second tubular segment 72 is a thermoplastic, such as high density polyethylene (which is a relatively lubricous, flexible and high strength material). One example of such a material is Marlex, HHM 4903, which is available from Phillips 66 Company, Houston, Tex. Such a tubular section may be formed by extrusion with thermal mechanical drawing to form a distal necked section. The interior of the second tubular segment 72 is also substantially hollow and defines an inflation lumen 126 extending from its proximal end 128 to its distal end 130 (see FIG. 4). HDPE is preferred since it is relatively lubricious. The lubricity may be further enhanced by coating the outer surface of the second tubular segment 72 with a silicone lubricant.

Figure 4:
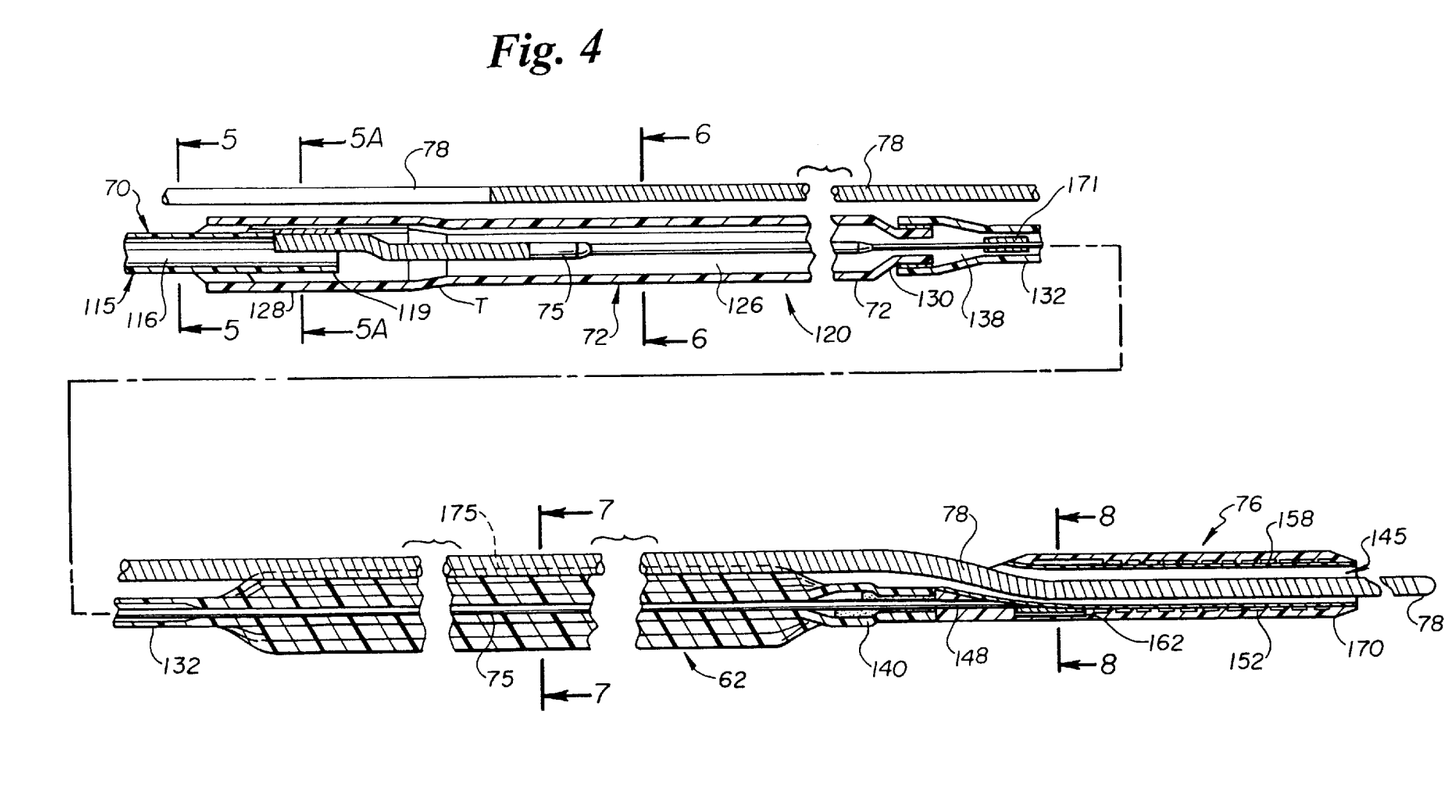
FIG. 4 is a longitudinal sectional view of portions of the angioplasty balloon catheter of FIG. 1.
Figure 5:
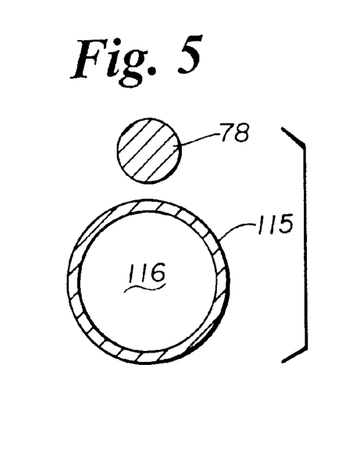
FIG. 5 is a sectional view taken along lines 5—5 in FIG. 4.

A proximal end 128 of the second tubular segment 72 extends over the distal end 119 of the metallic tube 115 and is attached thereto by a suitable bond (suitable sealing and bonding agents for this purpose include LOCTITE PRISM 405, a cyanoacrylate, available from Loctite Corp of Newington, Conn., or TRA-BOND 2135D, an epoxy available from Tra-Con, Inc. of Medford, Mass.). As best seen in FIG. 4, the inflation lumen 116 of the metallic tube 115 is connected with the inflation lumen 126 of the distal shaft section 120. The second tubular segment 72 of the distal shaft section 120 is necked down and bonded at its distal end 130 to a proximal waist or neck 138 of the balloon 62 by means of a suitable adhesive and sealing agent. Suitable bonding materials include LOCTITE PRISM 405, a cyanoacrylate, available from Loctite Corp. of Newington, Conn., TRA-BOND 2135D, an epoxy, available from Tra-Con, Inc. of Medford, Mass., or a urethane adhesive such as UR3507 available from H. B. Fuller of St. Paul, Minn.

The second tubular segment 72 is tapered distally from its relatively larger proximal end 128 to its smaller distal end 130. In an exemplary embodiment, the larger proximal end 128 of the second tubular segment 72 is approximately 2.25 inches long (measured from the distal end of the metallic tube 115 to the taper T in FIG. 4) and has a nominal outer diameter of approximately 0.031 in. and a nominal inner diameter of approximately 0.026 in. The smaller distal end 130 is approximately 9.5 inches long (measured from the taper T to a proximal waist 132 of the balloon 62) and has a nominal outer diameter of approximately 0.026 in. and a nominal inner diameter of approximately 0.021 in. The reduced diameter of the second tubular segment 72 is preferably achieved by a necking process and allows good flexibility and "trackability" for the balloon catheter 50 in the patient's vascular system. By injecting radiopaque dye into the guide catheter the arterial lumens are made visible on a fluoroscope. Reducing the diameter of the balloon catheter 50 (along the second tubular segment 72) allows more dye to flow adjacent and around the catheter 50, thus, making the lumen areas more visible which aids in the positioning of the balloon catheter 50 in the artery and in the evaluation of dilatation performance.

The core member 75 provides two related functions. First, it provides axial or column strength to the distal shaft section 120. Second, it prevents kinking of the distal shaft section 120. As discussed above, the metallic tube 115 defining the first tubular segment 70 is relatively stiff and the second tubular segment 72 is relatively flexible. Further, relatively stiff catheter sections are defined at both ends of the distal shaft section 120 by the metallic tube 115 at one end and the guide wire 78 and the guide wire lumen of the distal tip body 76 at the other end. Without the core member 75 extending therebetween, such a configuration would tend to buckle or bend in the relatively flexible area as an attempt is made to advance the catheter 50 through the vasculature. Responsiveness of the catheter would thus be substantially diminished. Further, the catheter 50 might tend to kink adjacent the shaft transition from the hypotube to the relatively more flexible plastic tube.

The core member 75 is a structural member which increases the stiffness of the distal shaft section 120. The core member 75 is less stiff (or has less axial strength) than the hypotube of the metallic tube 115, but is more stiff than the second tubular segment 72. The core member 75, however, is configured to be more trackable than the metallic tube 115. Thus, the combination distal shaft section 120 will preferably be more pushable than the second tubular segment 72 alone and yet more trackable than the first tubular segment 70 (metallic tube 115).

The core member 75 preferably provides varying flexibility along its length such that its flexibility increases in the distal direction. As illustrated in FIG. 4 (not shown to scale), this may be accomplished by defining the core member 75 as a core wire with one or more distal reductions in its outer diameter (formed e.g., by ground tapers). At its proximal end, the core member 75 has a diameter of approximately 0.012 in., while adjacent its distal end, the core member 75 has a diameter of approximately 0.0055 in. and is gradually flattened along its distal 0.150 in. to form a ribbon of 0.002 in. by 0.012 in. that is 0.03 to 0.05 in. long. It should be noted that the exemplary tapers of the core member 75 shown in FIG. 4 are exaggerated for clarity. The core member 75 is preferably formed of a high strength stainless steel or other high strength alloy such as 17-7PH stainless, 18-8PH stainless, and 300 or 400 Series stainless steel. In one embodiment, the core member 75 is formed from a core wire of Type 304 stainless steel and manufactured by centerless grinding.

Figure 5A:
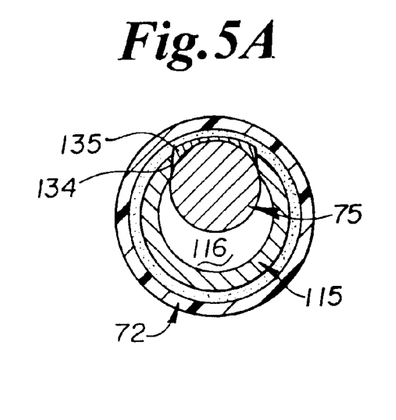
FIG. 5A is a sectional view taken along lines 5A—5A in FIG. 4.

The metallic tube 115 has a longitudinal slot 134 formed at its distal end 119 (FIGS. 4 and 5A). In a preferred embodiment, the slot 134 is about 0.011 inches wide (0.279 mm) and about 0.25 inches long (6.35 mm). A proximal end of the core member 75 is received within the slot 134 of the metallic tube 115, and connected thereto by a suitable bonding material 135. In a preferred embodiment, the bonding material 135 is a braze material composed of a silver brazing metal powder with a brazing flux, such as BAg-7-325 mesh available from Turbo-Braze, Corp. (Union, N.J.). Other bonding materials are also contemplated, such as a two-part braze of a flux (LR FLUX) from Lucas-Milhaupt of Mt. Vernon, N.Y., and a braze wire (Alloy #BAg-7) from California Fine Wire of Grover City, Calif. Alternatively, the core member 75 can be joined to the metallic tube 115 by a silver solder material composed of 4% silver and 96% tin. An adhesive material, such as cyanoacrylate, may be used to join a core member 75 to a metallic tube 115 composed of a super elastic alloy. The core member 75 is preferably stress-relieved by exposing it before grinding to a temperature in a range of from 500° F. to 800° F. for a period of about 30 minutes to about 6 hours, and preferably at 700° F. for about 5 hours including ramp-up time. Preferably, the core member 75 has a total length of 13.5 inches, but it will be appreciated that the dimensions and configurations of the core member 75 will vary depending upon the length of the distal shaft section for the catheter 50 (which may vary within a range of about 25 cm to about 35 cm, depending upon intended use).

Figure 6:
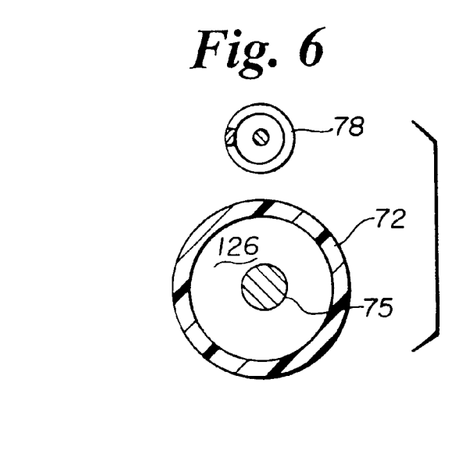
FIG. 6 is a sectional view taken along lines 6—6 in FIG. 4.

As seen in FIGS. 4 and 5A, the proximal end of the core member 75 is offset from the axis of the catheter 50, but assumes a generally central axial alignment distally of the connection of the core member 75 to the metallic tube 115, as it extends through the second tubular segment 72 (see FIG. 6). Again, it should be noted that the drawings are not to scale, but have been exaggerated for clarity (for example, in FIG. 4, the transition of the core member 75 from an off-axis connection to a generally coaxial alignment distally therefrom is much more gradual than shown and there is no permanent set curve placed in the core member 75).

As described, the metallic tube 115 of the first tubular segment 70 and the flexible polymer second tubular segment 72 cooperatively define the shaft 52 for the catheter 50. The relatively stiff metallic tube 115 of the first tubular segment 70 provides sufficient pushability for insertion of the catheter 50 into distal portions of the vasculature. The second flexible plastic tubular segment 72 provides sufficient flexibility for allowing the catheter 50 to track through the tortuous path of the coronary arteries and distal curves of the guide catheter 80 leading to the stenosis or obstruction. Furthermore, the core member 75 enhances the stiffness of the second tubular segment 72 to provide sufficient pushability for the second tubular segment 72, since the guide wire 78 does not extend within the second tubular segment 72 to provide longitudinal support thereto, but only along the very short distal guide wire lumen in the distal tip body 76 of the catheter 50. Because of the polymer construction of the second tubular segment 72, the core member 75 does not make the second tubular segment 72 prohibitively stiff or inflexible.

The Catheter Balloon

The balloon 62 extends distally from the second tubular segment 72 and forms a distal extent of the second tubular segment 72. The balloon 62 has an interior 138 in fluid communication with the interior 126 of the second tubular segment 72. A suitable balloon material is a polyolefin which has been treated by electron beam cross linking. A suitable polyolefin is available from E. I. Du Pont de Nemours & Co. of Wilmington, Del. under the trade name SURYLYN® (8527) Ionomer. The balloon 62 may also be coated with a silicone lubricant.

Figure 7:
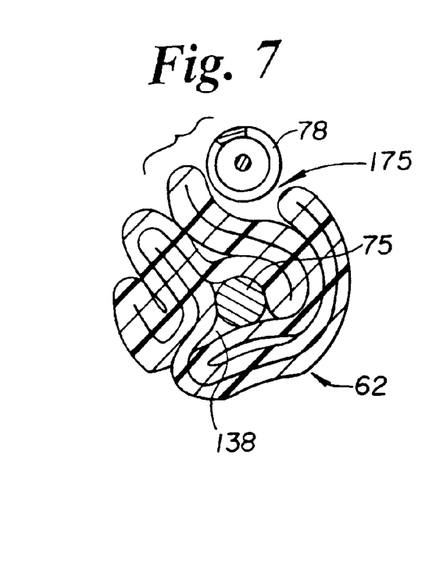
FIG. 7 is a sectional view taken along lines 7—7 in FIG. 4.
Figure 8:
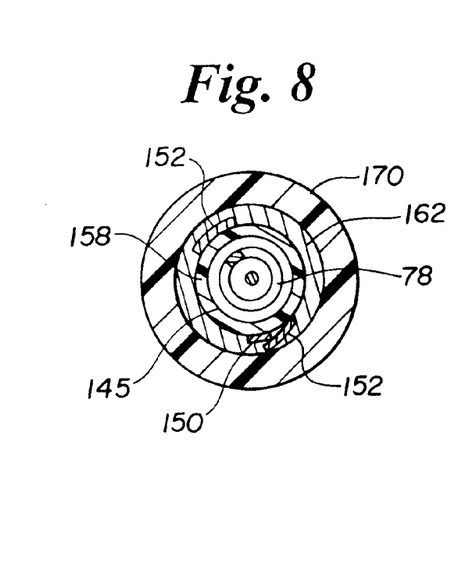
FIG. 8 is a sectional view taken along lines 8—8 in FIG. 4.

The core member 75 extends through the balloon 62 (see FIGS. 4 and 7). A distal waist or neck 140 of the balloon 62 is sealably connected to the core member 75 by a suitable adhesive and sealing material such as LOCTITE PRISM 405, a cyanoacrylate, available from Loctite Corp. of Newington, Conn., or TRA-BOND 2135D, an epoxy available from Tra-Con, Inc. of Medford, Mass.

Figure 9:
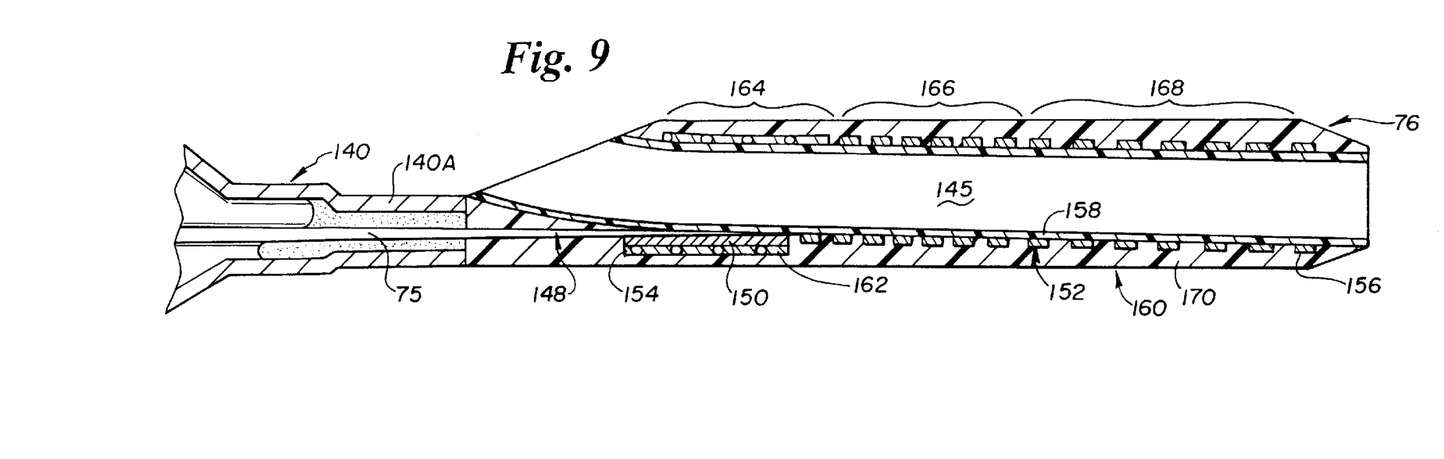
FIG. 9 is an enlarged longitudinal sectional view of the distal tip of the catheter of FIG. 4.

The balloon length will vary depending upon the desired size of the dilatation catheter, but typical lengths are 20 to 50 mm. Further, typical preferred inflated dilatation diameters for the balloon are 1.5 to 4 mm. In a preferred embodiment, the proximal waist 132 of the balloon is approximately 13 mm long, the expandable portion of the balloon (body 62a and cone portions 62b and 62c as seen in FIG. 9) is approximately 21–28 mm long (depending on the desired balloon inflated diameter) and distal waist 140 of the balloon is approximately 1.5 to 3 mm long. In an alternative embodiment, the proximal waist 132 may extend all the way to the tube 115, thereby defining the proximal extent of the second tubular segment 72.

The Distal Tip Body

The distal tip body 76 defines a short guide wire lumen 145 therethrough. A preferred embodiment of the tip body 76 is illustrated in FIGS. 4, 8, 9 and 10. A distal portion 148 of the core member 75 extends distally from the distal balloon waist 140. As mentioned above, the distal end of the core member 75 is flattened to a flat ribbon section 150.

The tip body 76 includes a coil 152 having a proximal end 154 and a distal end 156. The distal section 150 of the core member 75 is connected to the coil 152 adjacent its proximal end 154. A tubular liner 158 of lubricious polymer material is positioned within the coil 152 to define the guide wire lumen 145 therethrough. The distal portion 148 of the core member 75, coil 152 and liner 158 are all encased by a plastic cover 160 to provide a smooth outer exterior for the distal tip 76 and to facilitate bonding of those components together and to the catheter 50.

The coil 152 is preferably formed from a radiopaque material such as a radiopaque platinum alloy. Preferably, the coil has a length of approximately 7 mm and is formed from a ribbon having dimensions of 0.0015 inches by 0.004 inches. Although the preferred embodiment uses a coil material having radiopaque characteristics, other materials may also suffice, such as stainless steel or Kevlar. A platinum alloy ribbon of this type is available from Sigmund Cohn Corporation of Mount Vernon, N.Y. In one preferred embodiment, a proximal portion of the coil 152 has its coils spaced approximately 0.001 inches apart, with a 0.005 pitch, while the remaining distal portion of the coil has its coils spaced approximately 0.004 inches apart, with a 0.008 pitch. Accordingly, the distal portion of the coil 152 has a reduced metallic component thereto and enhanced flexibility. Before assembly, the coil 152 is wound to have an inner diameter of approximately 0.019 inches.

The distal ribbon section 150 of the core member 75 is preferably bonded to a proximal portion of the coil 152 by a braze material. A suitable braze is achieved using a silver brazing metal powder with a brazing flux, such as BAg-7-325 mesh available from Turbo-Braze Corp. of Union, N.J. Alternatively, the core member 75 can be joined to the coil 152 by a silver solder material composed of 4 percent silver and 96 percent tin.

To assemble the core member 75 to the coil 152, a titanium mandrel having an outer diameter of approximately 0.0195 inches is used. The mandrel (not shown) is inserted into the coil. Several proximal coils of the coil 152 are then rotated to expand the coil and the flattened distal segment 152 is inserted between the mandrel and those rotated coils. The coils are then relaxed over the inserted flattened segment 150 and the mandrel. Braze material is then applied to that section of the coil 152 adjacent the flattened segment 150 of the core member 75. The braze material does not adhere to the titanium mandrel, and flows around the coils and fills in the spacings between adjacent coils for the most proximal four to five coils of the coil 152, as illustrated in FIG. 9 by braze material 162. After curing, the titanium mandrel is then withdrawn and the result is a relatively solid tube of metallic material for a proximal portion of the coil 152 which is defined by the several proximal coils, braze material 162 and flat ribbon segment 150. The inner diameter of the coil 152 along its entire length is maintained at about 0.019 inches by the mandrel. In this manner, the preferred coil structure thus has three segments (FIG. 9) of differing flexibility along its length: (1) a proximal segment 164 embedded in braze material 162, (2) an intermediate segment 166 wherein the coil spacings are relatively close together, and (3) a distal segment 168 wherein the coil spacings are expanded for adjacent coils. The braze material 162 is applied to extend at least from the distal tip of the flat ribbon segment 150 to the proximal end 154 of the coil 152, typically 0.03 inches to 0.05 inches. This results in a relatively strong bond between the core member 75 and the coil 152. The braze material 162 further assists in defining a radiopaque marker for the catheter adjacent its distal tip in the coil section 164.

The liner 158 is provided to minimize friction between the guide wire lumen 145 and guide wire 78 in the device 76. Preferably, the liner 158 is formed from a polytetrafluoroethylene (PTFE or TEFLON) tube. A TEFLON tube suitable for this purpose is a natural polytetrafluoroethylene material obtained from Fluortech Medical Incorporated of Easton, Pa. The tube as obtained from this source has an inner diameter of 0.017 to 0.020 inch tolerance and an outer diameter of 0.023 to 0.026 inch tolerance. The tube parameters are then altered by a conventional neck down process to a desired outer diameter of 0.019 inches, a wall thickness of 0.0015 inches, and an inner diameter of 0.016 inches (in order to adequately accommodate a typical angioplasty guide wire having an outer diameter of 0.014 inches). TEFLON is a desired material because it is very flexible and lubricous, and can be formed with very thin walls, although other materials such as polyethylene are also contemplated. The exterior of the Teflon tube is chemically etched to promote adhesion of the liner 158 to the other components of the distal tip body 76. The TEFLON tube is dipped into a suitable chemical etching material for about five seconds, rinsed off and then ultrasonically cleaned. A suitable material for this purpose is Tetra-Etch of W. L. Gore and Associates, Inc., of Flagstaff, Ariz. This chemical etching process strips fluorine atoms from the surface of the TEFLON tube and replaces them with hydrogen and oxygen atoms to enhance the surface of the tube for adhesion.

The distal portion 148 of the core member 75, coil 152 bonded thereto, and TEFLON liner 158 are all coated exteriorly with an outer coating of urethane 170. This coating not only encases the coil 152, but bonds the liner 158 to the coil 152 as well. The urethane coating 170 smooths the exterior of the tip body 76 to keep the coil 152 from possibly snagging, stretching or breaking in use.

The assembly of a catheter having a distal tip 76 as described above involves the following general assembly steps. The proximal portions of the catheter are formed and assembled, with the metallic tube 115 bonded to the core member 75. The second tubular segment 2 is bonded to the balloon 62, and that assembly is then slipped onto the metallic tube/core member assembly from the distal end of the core member 75. The tubular segment/balloon assembly is slipped proximally over the metallic tube/core member assembly and is not yet bonded thereto. The coil 152 is then secured to the distal flattened tip of the core member 75. The tubular segment/balloon assembly is then moved distally and the distal waist 140 of the balloon 62 is bonded to the core member 75 (as seen in FIG. 9, the distal waist 140 of the balloon 62 may be further reduced in internal diameter as at 140a to enhance bonding to the core member 75). The proximal end of the tubular segment 72 is then bonded to the distal end of the metallic tube 115 to fully define the sealed inflation path for the catheter's balloon. A segment of the Teflon tube for forming the liner 158 is then inserted into the coil 152. For assembly purposes, this segment is about one to two inches long (longer than the coil 152) and is pinched off at its ends to seal off the interior of the liner 158. If desired, the Teflon tube segment may be adhered to the coil 152 at the braze area or proximal end of the coil by a suitable adhesive such as LOCTITE PRISM 405, a cyanoacrylate, available from Loctite Corp. of Newington, Conn.

Once the TEFLON tube segment is aligned within the coil 152, the catheter assembly is then ready for application of the urethane coating 170 to the distal tip 76. The ends of the liner 158 are pinched off to prohibit urethane from entering into the interior of the liner 158 during urethane coating application. The urethane coating 170 is either solvent cast in place, or applied using a two-part polyurethane. In a solvent-casting process, a bath of solvent with urethane dissolved therein is provided, and the distal portion of the catheter assembly is dipped in this bath. As the solvent dries, the urethane remains. It may take five or six coats to build up a suitable depth of urethane to provide the smooth outer surface and adhesive ability desired by the urethane coating 170. An alternative means for applying the urethane coating is to use a two-part polyurethane, such as TecoFlex material from Thermedics, Incorporated of Woburn, Mass. One advantage of this type of urethane application is that there is no solvent involved, and thus as the urethane cures, it does not lose any volume. Thus, only one dip or application of material is necessary. However, it may be more necessary to smooth out a two-part polyurethane type coating to obtain the desired profile for the distal tube 76. Such forming of the exterior of the coating may be done either by use of a peel-away polymer or Teflon tube mold, or by a drawing process. The use of a mold is preferred, where the mold (which would provide a mold cavity of the desired outer configuration for the distal tip 76) is positioned about the distal tip and the polyurethane material is then injected into the mold cavity. Once the polyurethane has cured, the mold is then removed. If a drawing process is used, the distal tip 76 is drawn through a die to achieve a desired outer diameter for the distal tube 76.

After the urethane coating 170 has been applied and cured to its desired thickness (using either application method), the ends of the distal tip 76 are cut to their desired shape. In FIG. 9, it is seen that the distal tip of the tip body 76 is tapered or rounded and cut off to expose a distal opening for the guide wire lumen 145. The tapering is to facilitate ease of advancement of the catheter, and to minimize the possibility for vessel trauma. Likewise, the proximal end of the tip body 76 is cut and shaped as desired to provide a proximal opening for the guide wire lumen 145. The liner 158 (and accordingly guide wire lumen 145) is canted slightly away from the core member 75 at the proximal end of the tip body 76, as best seen in FIG. 9. This facilitates withdrawal of the catheter 50, for example, by minimizing the possibility of snagging or catching the tip body 76 on the distal end of the guide catheter. Preferably, the guide wire lumen is approximately eight mm long, although any length up to two cm is contemplated.

Prior to assembly, some of the components of the catheter are preferably plasma treated using helium or oxygen plasma treating techniques to increase their bonding characteristics. Such components may include, for example, the polyethylene and polycarbonate components of the catheter including the catheter manifold (mating member 54), the second tubular segment (72), etc., as well as other components such as any radiopague marker bands, and the metallic tube 115 and core member 75 assembly.

The resultant tip body 76 is firmly bonded to the core member 75 and to catheter 50 and provides a flexible, lubricious and thin-walled guide wire lumen at the distal tip of the catheter 50. When a radiopaque material is used for the coil 152, the tip body 76 further provides a radiopaque marker band for the catheter 50.

Preferably, a second marker band 171 (FIG. 4) is affixed to the core member 75 proximally of the balloon 62, in a symmetrical manner relative to the longitudinal center of the balloon 62 with coil 152. Thus, a physician can observe those two marker bands by fluoroscopy, knowing that the balloon 62 is centered therebetween. Alternatively, a marker band may be positioned on the core member 75 at the longitudinal center of the balloon 62, as indicated by marker band B shown in phantom in FIG. 10.

The resultant tip body is thus a composite design, having a radiopaque platinum alloy coil surrounded on both sides by a polymer. The coil is firmly brazed to the core wire, and the function of the polymer is to cover the coil, making the end of the tip very flexible and providing a lubricious surface for good wire movement. The coil functions to give the tip an intermediate stiffness where it extends past the brazed area. Furthermore, the coil keeps the thin-walled tip from kinking as it deflects around bends (or in the physician's hands). Alternative coil designs are also contemplated such as, for example, leaving the spacing of adjacent coils (and pitch) the same along the entire coil length, or uniformly varying the spacing of adjacent coils and therefore the pitch of the coil as it extends distally.

The radiopacity of the distal tip of the catheter 50 is also important to permit the physician to locate the distal tip of the catheter 50 and thus avoid inadvertent advancement of the catheter 50 over the distal end of the guide wire 78. This would, of course, result in the loss of the ability of the catheter 50 to track the path of the guide wire 78.

Figure 10:
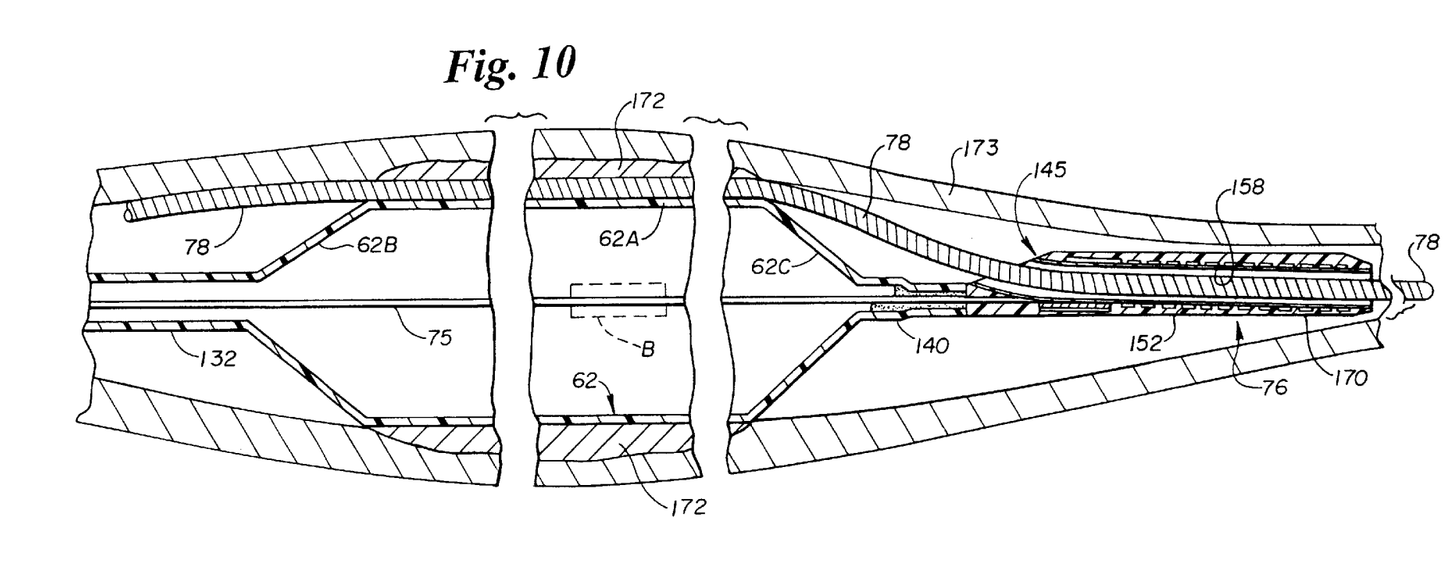
FIG. 10 is a longitudinal sectional view of the angioplasty balloon catheter of FIG. 1, shown dilating a stenosis in a patient's vasculature.

FIG. 10 illustrates the catheter 50 with its balloon 62 inflated adjacent a lesion 172 in a stenosed vascular lumen 173. The guide wire 78 extends along the catheter exteriorly of the balloon 62, and thus when the balloon 62 is inflated, the guide wire 78 also presses against and dilates the lesion 172. The distal portion of the guide wire 78, however, remains in place through the guide wire lumen 145 of the distal tip 76 on the catheter 50.

Figure 11:
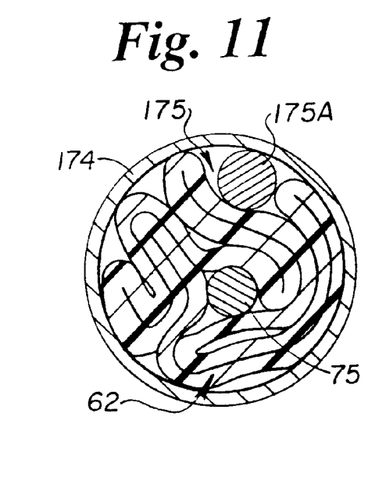
FIG. 11 is a lateral sectional view of the folded and wrapped balloon of the inventive catheter, with balloon protector and possible shipping mandrel in place.

After the catheter has been completely assembled, a tubular balloon protector is applied over the balloon 62. In FIG. 11, this balloon protector is shown as protector 174.

Although the guide wire 78 is external to the balloon 62 during use, the balloon 62 may optionally be formed, in its initial deflated state, to readily accommodate the guide wire 78 alongside thereof. In this instance, as seen in FIGS. 4 and 7, the balloon 62, in its uninflated and folded state, has a longitudinal trough 175 defined therein which is adapted to receive the guide wire 78. This trough 175 is, for the most part, defined by the pre-use protective packaging assembly which is provided for the balloon. A short (0.5 to 0.75 inch) shipping mandrel (not shown) of about 0.016 inch diameter is also inserted into the guide wire to protect the distal tip of the catheter during sterilization, packaging, shipping and pre-use handling. Before application of the balloon protector 174, however, a longer shipping mandrel 175a (formed from a stainless steel wire having an outer diameter of about 0.015 inches) is inserted into the guide wire lumen and then laid alongside the deflated balloon 62. Application of the balloon protector 174 aids in forming the balloon 62 against the shipping mandrel 175a to define the trough 175. In use, the balloon protector 174 and shipping mandrel 175a are removed, but the deflated balloon 62 retains the trough 175 for accommodating the guide wire 78 (see FIGS. 4 and 7).

Although the inventive catheter described and illustrated herein is shown in reference to a balloon dilatation catheter for stenosis treatment, other stenosis reducing mechanisms may also be used. For example, the intralumenal device for reducing or ablating the stenosis may be an atherectomy-type cutter, a laser device, a water jet device and sonic or ultrasonic therapeutic devices. The present invention may also be used with other interoperative devices such as drug delivery devices, ultrasonic imaging devices and perfusion devices.

Alternative Distal Tin Body Constructions

Numerous alternative embodiments of the distal tip body of the present invention are contemplated. For example, several alternative arrangements for the tip body are illustrated and discussed herein, but it is not intended that the illustrated embodiments are all inclusive of those structures and designs which are included within the spirit and scope of the present invention. In the following discussion of further alternative embodiments of the present invention, to the extent a component is identical to that of the previously described embodiment, like reference numerals are used.

Figure 12:
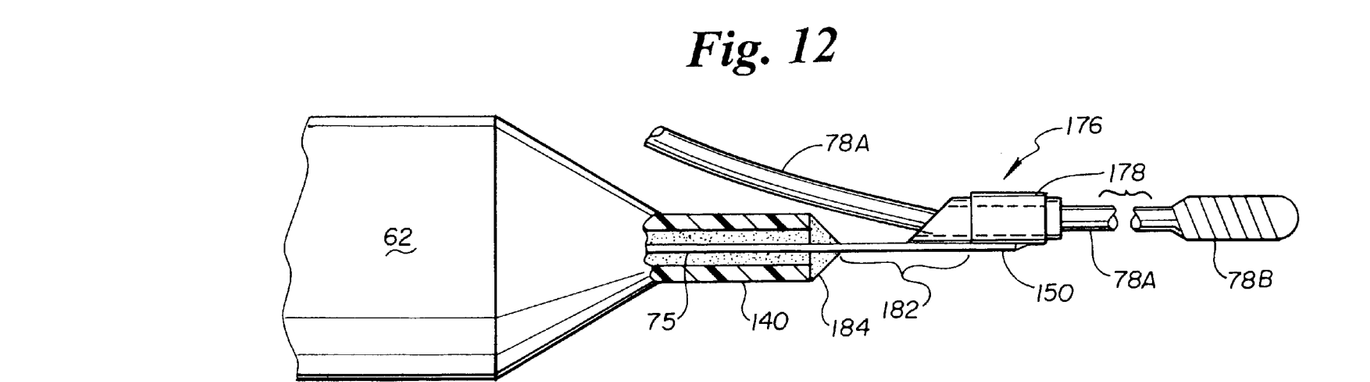
FIG. 12 is a longitudinal view (with some portions shown in section) of the distal portion of a second embodiment of the catheter of the present invention.
Figures 13, 14:
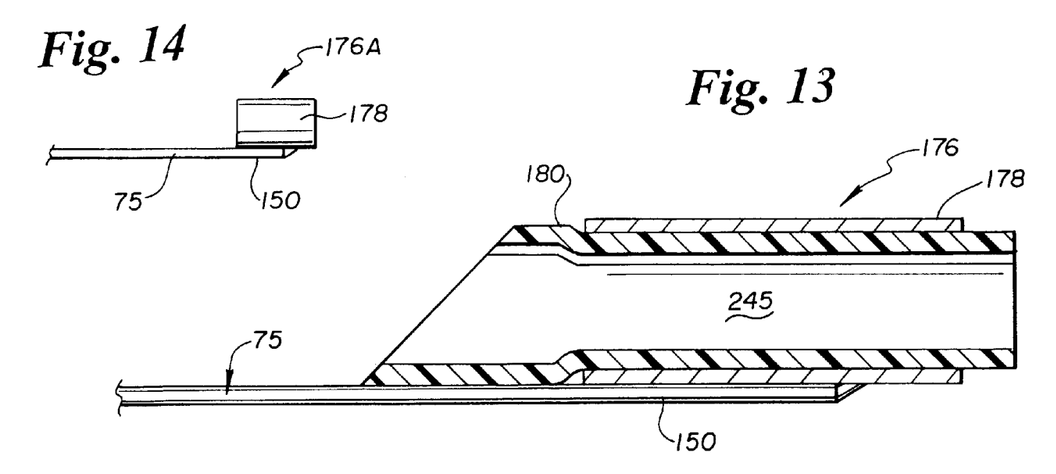
FIG. 13 is an enlarged longitudinal sectional view of the distal tipof the catheter of FIG. 12.
FIG. 14 is a longitudinal view of an alternative distal tip for the catheter of the present invention.

In FIGS. 12 and 13, a tip body 176 is illustrated. Except where otherwise noted, the construction of the catheter is similar in this and further embodiments. In the embodiment of FIGS. 12 and 13, the core wire 75 is again tapered to a small distal diameter and ultimately into a flat ribbon segment 150. The tip body 176 is formed essentially from a very short (e.g., about 0.05 inch) metal tube 178 bonded to the flat ribbon segment 150. Preferably, the metal tube 178 is formed from a radiopaque material, and also serves as a distal marker band for the catheter. The flat ribbon 150 is secured to the metal tube 178 on the outside of the metal tube 178. These components are affixed together by a suitable braze or solder joint as described above, along all contiguous points therebetween to form a secure bond.

A lubricious plastic liner 180 (e.g., polyethylene or Teflon) is fixed within the metal tube 178 by a suitable adhesive. The liner 180 extends beyond the metal tube 178 at its proximal and distal ends, with the exposed ends of the liner shaped as desired. The liner 180 is preferably about 0.10 inch long and extends out each end of the metal tube 178 about an equal distance (although a liner of up to 0.25 inch is contemplated). For instance, the distal tip of the liner 180 may be tapered to provide an atraumatic tip for the tip body 176, and the proximal end of the liner 180 may be cut away as shown in FIGS. 12 and 13 to facilitate catheter withdrawal without snagging or catching on the guide catheter. The liner 180 thereby defines a short guide wire lumen 245 for the catheter, with the guide wire lumen 245 being entirely distal of the catheter balloon 62 or other interoperative components of the catheter.

As illustrated in FIG. 12, a portion 182 of the core member 75 is exposed between the distal balloon waist 140 and the metal tube 178. This permits the tip body 176 to be highly flexible relative to the remainder of the catheter. In order to provide a smoother transition between the exposed portion 182 of the core member 75 and the distal balloon waist 140, adhesive material 184 is backfilled about the core member 75, as shown in FIG. 12. The resultant tip body 176 is very flexible relative to the catheter, provides the necessary short distal guide wire lumen to allow the catheter to track a guide wire 78A and is relatively simple to manufacture. Although not shown, it is also contemplated that a urethane coating can be provided for the exposed portions of the tip body 176 to provide smoother outer surfaces for the tip body and cover the body with a lubricious material.

An alternative to the tip body 176 shown in FIGS. 12 and 13 is illustrated as tip body 176A in FIG. 14. In this embodiment, no plastic liner 180 is provided, and the tip body construction is otherwise the same as tip body 176.

It is contemplated that a tip body 176 or 176A has an effective guide wire lumen diameter of suitable size to accommodate a guide wire of 0.014 in. It is possible to make the lumen size as small as 0.010 in. for use with a guide wire having an outer diameter of less than 0.010 in. Such a small guide wire lumen is possible with this design, although a specific guide wire must then be provided for such use. It is contemplated that such a guide wire would be a smooth, solid strand with only a small coil on its distal tip to provide an atraumatic tip for the guide wire (see tip 78B on guide wire 78A in FIG. 12). The coil on tip 78B may have a larger diameter than the inner diameter of the tip body 176 so that the guide wire cannot be withdrawn. This prevents inadvertent advancement of the catheter off of the guide wire. The wire strand would possibly be coated with a lubricious material. A catheter having a tip design 176 in combination with a specifically designed guide wire 78A presents a more symmetrical dilatation profile in use—there is less of a "bump" (the guide wire) alongside the balloon. Such a specific guide wire would have an extra-low profile (about 0.006 in.) at those portions of the guide wire intended to run alongside the balloon to minimize the possibility of vessel trauma caused by the inflation of the balloon against the wire (and in turn against the lesion) during an angioplasty procedure. In the designs illustrated in FIGS. 12–14, a second marker band (not shown) is again provided on the core member 75 proximally of the balloon 62, with the second marker band and the metal tube 178 aligned symmetrically relative to the longitudinal center of the balloon 62 (or a marker band may be longitudinally centered within the balloon).

Figures 15, 16, 17, 18, 19:
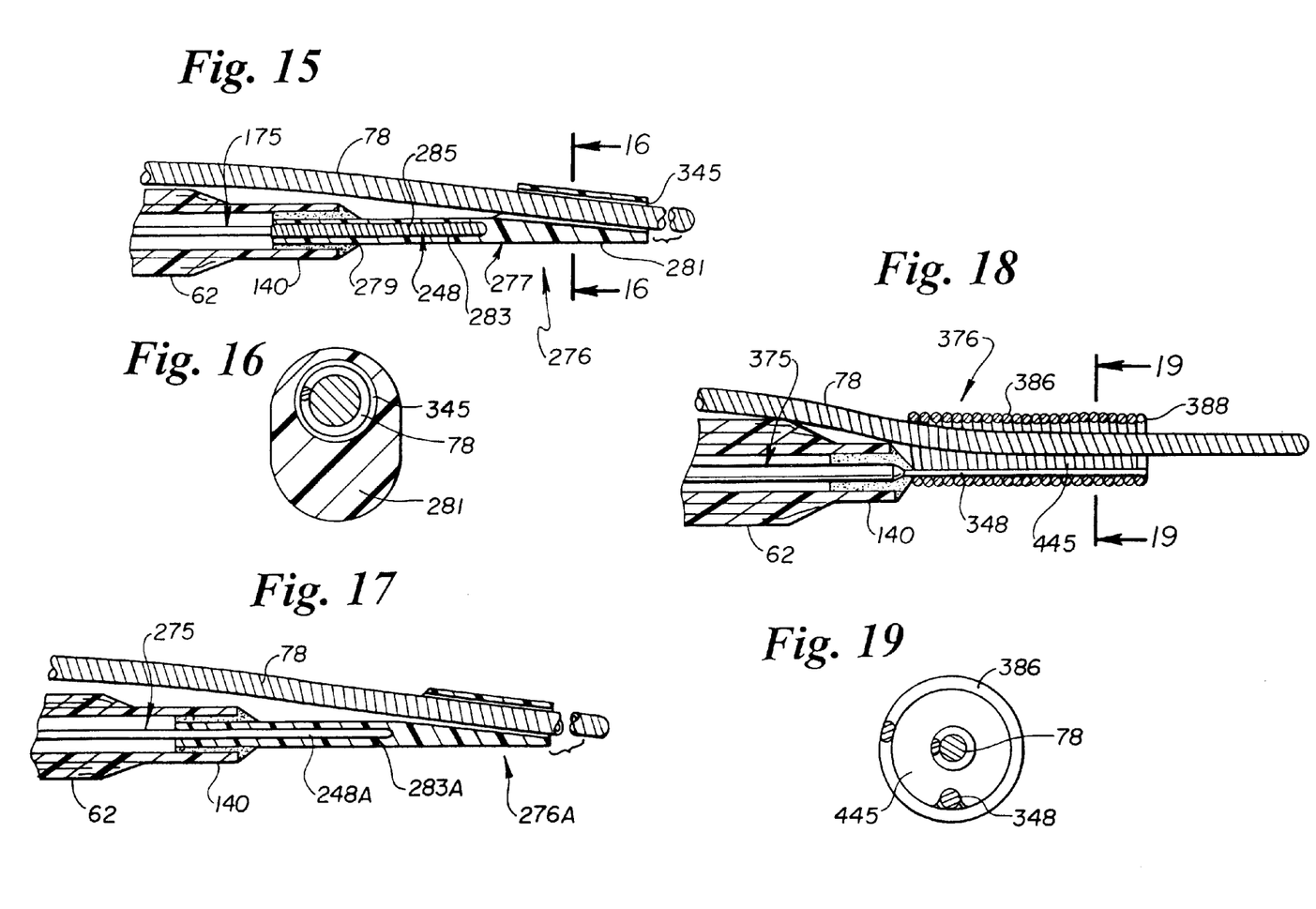
FIG. 15 is a longitudinal sectional view of the distal portion of another embodiment of the catheter of the present invention.
FIG. 16 is a sectional view as taken along lines 16—16 in FIG. 15
FIG. 17 is a longitudinal view of an alternative distal tip for the catheter of the present invention.
FIG. 18 is a longitudinal sectional view of the distal portion of another embodiment of the catheter of the present invention.
FIG. 19 is a sectional view as taken along lines 19—19 in FIG. 18.

Another embodiment for the tip body of the present invention is illustrated in FIGS. 15 and 16. In this embodiment, a tip body 276 is defined by a polymer body 277 which has a proximal section 279 and a distal section 281. The proximal section 279 has a bore 283 adapted for reception of a distal section 248 of a core member 175. A coil 285 is affixed to the distal section 248 of the core member 175, from the distal tip of the core member 175 to and through the balloon waist 140. The bore 283 of the tip body 276 is adapted to closely receive the coil 285 on the core member 175 and is bonded thereto by a suitable adhesive along its entire length within the coil 285. The proximal section 279 of the columnar body 277 is bonded to the balloon waist 140 by a suitable adhesive and sealing agent to seal off the distal end of the balloon 62 and to join the core member 175 to the balloon 62. On the distal section 281 of the polymer body 277, a longitudinal tube is provided to define a guide wire lumen 345. As illustrated, the tube is canted relative to the catheter axis to facilitate guide wire movement therethrough. The distal and proximal ends of the tube are formed as previously described to facilitate catheter advancement and withdrawal. The guide wire lumen 345 is preferably about eight mm long, and can extend up to about 2 cm in length.

FIG. 17 illustrates a modified embodiment 276A of the tip body shown in FIGS. 15 and 16. The tip body 276A is the same as that shown in FIG. 15, except no coil is provided on the distal section 248A of the core member 275. The core member 275 is received within a bore 283A in the tip body 276A and a distal portion 248A of the core member 275 is fitted therein and bonded thereto by a suitable adhesive.

In the tip body embodiments illustrated in FIGS. 15–17, the polymer body is preferably formed from polyurethane, Pebax material or ethylene vinyl acetate. In these versions of the tip body, the tip body itself does not provide a radiopaque marker. Accordingly, one or more marker bands are affixed about the core member as typical (e.g., a marker band may be positioned at the longitudinal center of the balloon).

Another embodiment of the tip body of the present invention is illustrated in FIGS. 18 and 19. This embodiment again employs a coil to define the guide wire lumen of the catheter. A tip body 376 has a spring coil 386 with its coils wound contiguously. A core member 375 tapers down and has a distal portion 348 extending distally beyond the balloon waist 140. As illustrated in FIG. 19, the distal portion 348 of the core member 375 has a round diameter, although the distal portion 348 may be flattened to a ribbon as previously described. The distal portion 348 of the core member 375 extends along an inner surface of the spring coil 386 (along the entire length of the spring coil 386, as illustrated in FIG. 18), and these components are bonded together by a suitable braze or solder connection along their entire contiguous portions. The catheter is thus provided with an atraumatic spring tip, and if desired, the distal portion 348 of the core member 375 could be shaped or bent to allow the catheter to be steered and advanced without regard to a separate guide wire. However, as defined, the spring coil 386 thus provides a guide wire lumen 445 for slidable reception of the guide wire 78 (preferably, the guide wire lumen is one to two cm in length). Preferably, the spring coil 386 is coated on its inner and outer surfaces by a lubricious material to facilitate movement of the catheter relative to the guide wire 78, the guide catheter and the vasculature. It is further contemplated that the spring coil 386 have its windings wound in the opposite direction from the windings of the distal portion of the guide wire 78 in order to minimize the possible catching or "ratcheting" of those coils as one component is moved relative to the other. Further, a bulbous tip 388 is provided on a distal end of the spring coil 386 to provide an atraumatic tip for the catheter.

Conclusion

The inventive catheter disclosed herein is a catheter structure with a short distal guide wire lumen. The use of a hypotube-type main shaft for the catheter allows the attainment of a high strength, flexible shaft having thin walls and a small diameter. The core member provides the catheter with sufficient pushability in its distal catheter section from the hypotube main shaft to the short distal guide wire lumen on the distal tip of the catheter, distally of any interoperative portions or members on the catheter. The core member also provides a more gradual transition between the relatively stiff main catheter shaft and the relatively flexible distal section of the catheter shaft. The distal shaft section has good pushability while still being quite trackable. The inventive catheter of the present invention has the ability to track a path already established by a guide wire within a patient's vasculature while being quite pushable and trackable. The inventive catheter allows for easy exchanges in a single-operator angioplasty device.

Although the present invention has been described with reference to preferred embodiments, workers skilled in the art will recognize that changes may be made in form and detail without departing from the spirit and scope of the invention.

What is claimed is:

1. A catheter comprising:

a first elongate shaft having a longitudinal axis and a distal end;

a balloon disposed proximate the distal end of the shaft;

a second elongate shaft extending distally of the balloon, the second shaft having a distal end;

a distal tip body secured to said second shaft distal end, said tip body including a short guide wire lumen therein which is adapted to slidably receive a guidewire therethrough said distal tip body having a cylindrical side surface and a proximal end surface;

said guidewire lumen having an axis, said axis being canted relative to said shaft longitudinal axis, said guidewire lumen having a guidewire lumen inlet and an outlet disposed distally of the balloon, and wherein the guidewire lumen inlet is disposed in said protinal end surface.

2. A catheter as recited in claim 1, wherein said distal tip body further comprises a tube defining said guidewire lumen.

3. A catheter as recited in claim 1, wherein said guidewire lumen includes a lubricous inner wall.

4. A catheter as recited in claim 1, wherein said shaft includes a lumen.

5. A catheter as recited in claim 4, wherein said catheter is an angioplasty catheter and said shaft lumen defines an inflation lumen in fluid communication with said balloon.

6. A catheter as recited in claim 5, wherein said catheter includes a proximal portion including hypotube.

\* \* \* \* \*

UNITED STATES PATENT AND TRADEMARK OFFICE
CERTIFICATE OF CORRECTION

PATENT NO. : 5,921,958
DATED : July 13, 1999
INVENTOR(S) : Ressemann et al.

It is certified that error appears in the above-identified patent and that said Letters Patent is hereby corrected as shown below:

Column 18, line 24, delete "protinal", insert --proximal--.

Signed and Sealed this

Second Day of May, 2000

Attest:

Q. TODD DICKINSON

*Attesting Officer*

*Director of Patents and Trademarks*